(12) United States Patent
Eisinger

(10) Patent No.: US 11,571,192 B2
(45) Date of Patent: Feb. 7, 2023

(54) ADAPTER ASSEMBLY FOR SURGICAL DEVICES

(71) Applicant: Covidien LP, Mansfield, MA (US)

(72) Inventor: Joseph T. Eisinger, Northford, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/464,092

(22) Filed: Sep. 1, 2021

(65) Prior Publication Data

US 2022/0096068 A1 Mar. 31, 2022

Related U.S. Application Data

(60) Provisional application No. 63/083,243, filed on Sep. 25, 2020.

(51) Int. Cl.
*A61B 17/064* (2006.01)
*A61B 17/00* (2006.01)
(Continued)

(52) U.S. Cl.
CPC .......... *A61B 17/00* (2013.01); *A61B 17/1155* (2013.01); *A61B 2017/0046* (2013.01);
(Continued)

(58) Field of Classification Search
CPC ................ A61B 17/00; A61B 17/1155; A61B 2017/0046
See application file for complete search history.

(56) References Cited

U.S. PATENT DOCUMENTS 2,957,353 A 10/1960 Babacz
3,111,328 A 11/1963 Di Rito et al.
(Continued)

FOREIGN PATENT DOCUMENTS

CA 2451558 A1 1/2003
CN 1547454 A 11/2004
(Continued)

OTHER PUBLICATIONS

Extended European Search Report corresponding to International Application No. EP 14 18 4882.0 dated May 12, 2015.
(Continued)

*Primary Examiner* — Eyamindae C Jallow
(74) *Attorney, Agent, or Firm* — Carter, DeLuca & Farrell, LLP

(57) ABSTRACT

An adapter assembly for operably connecting an end effector to a handle assembly includes a first drive assembly. The first drive assembly includes a first connector drive shaft configured to be rotated at a first speed, a first proximal worm gear in operable engagement with the first connector drive shaft, a first distal worm gear in operable engagement with the first proximal worm gear, and a first drive connector in operable engagement with the first distal worm gear. The first proximal worm gear and the first distal worm gear are configured to rotate the first drive connector at a second speed which is less than the first speed. The adapter assembly may include a second drive assembly which is substantially similar to the first drive assembly.

20 Claims, 5 Drawing Sheets

(51) Int. Cl.
*A61B 17/115* (2006.01)
*A61B 17/072* (2006.01)

(52) U.S. Cl.
CPC .............. *A61B 2017/00486* (2013.01); *A61B 2017/07257* (2013.01); *A61B 2017/07271* (2013.01); *A61B 2017/07285* (2013.01)

(56) References Cited

U.S. PATENT DOCUMENTS

| | | | |
|---|---|---|---|
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,141,049 B2 | 11/2006 | Stern et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,246,734 B2 | 7/2007 | Shelton, IV | |
| 7,252,660 B2 | 8/2007 | Kunz | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |

(56) References Cited

U.S. PATENT DOCUMENTS

| | | |
|---|---|---|
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 * | 10/2012 | Bryant ............... A61B 17/0686 227/19 |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,597,104 B2 * | 3/2017 | Nicholas ............... A61B 17/32 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |

(56) References Cited

U.S. PATENT DOCUMENTS

| | | |
|---|---|---|
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

(56) References Cited

U.S. PATENT DOCUMENTS

| | | | | |
|---|---|---|---|---|
| 2018/0021042 | A1* | 1/2018 | Nicholas | A61B 17/07207 227/175.2 |
| 2018/0125594 | A1* | 5/2018 | Beardsley | A61B 17/07207 |
| 2019/0125342 | A1* | 5/2019 | Beardsley | A61B 17/07207 |

FOREIGN PATENT DOCUMENTS

| | | | |
|---|---|---|---|
| CN | 1957854 | A | 5/2007 |
| CN | 101495046 | A | 7/2009 |
| CN | 101856251 | A | 10/2010 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1759652 | A2 | 3/2007 |
| EP | 1769754 | A1 | 4/2007 |
| EP | 1908412 | A2 | 4/2008 |
| EP | 1917929 | A1 | 5/2008 |
| EP | 1952769 | A2 | 8/2008 |
| EP | 2090247 | A1 | 8/2009 |
| EP | 2245994 | A1 | 11/2010 |
| EP | 2316345 | A1 | 5/2011 |
| EP | 2377472 | A1 | 10/2011 |
| EP | 2668910 | A2 | 12/2013 |
| EP | 2815705 | A1 | 12/2014 |
| ES | 2333509 | A1 | 2/2010 |
| FR | 2861574 | A1 | 5/2005 |
| JP | 2005125075 | A | 5/2005 |
| KR | 20120022521 | A | 3/2012 |
| WO | 2011108840 | A2 | 9/2011 |
| WO | 2012/040984 | A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Notification of Transmittal of the International Search Report and the Written Opinion of the International Searching Authority issued in corresponding application No. PCT/US2016/027042 dated Jul. 12, 2016.

* cited by examiner

ADAPTER ASSEMBLY FOR SURGICAL DEVICES

CROSS-REFERENCE TO RELATED APPLICATION

This application claims the benefit of and prior to U.S. Provisional Patent Application No. 63/083,243, filed on Sep. 25, 2020, the content of which is incorporated herein by reference in its entirety.

FIELD

This disclosure relates generally to adapter assemblies for selectively connecting an end effector to an actuation unit of powered surgical devices. More particularly, this disclosure relates to adapter assemblies having at least one drive assembly with multiple worm gears.

BACKGROUND

Powered devices for use in surgical procedures are known. To permit reuse of the handle assemblies of these powered surgical devices and to allow use of the handle assembly with a variety of end effectors, adapter assemblies and extension assemblies have been developed for selective attachment to the handle assemblies and to a variety of end effectors. Following use, the adapter and/or extension assemblies may be disposed of along with the end effector. In some instances, the adapter assemblies and extension assemblies may be sterilized for reuse.

SUMMARY

An adapter assembly for operably connecting an end effector to a handle assembly includes a first drive assembly. The first drive assembly includes a first connector drive shaft configured to be rotated at a first speed, a first proximal worm gear in operable engagement with the first connector drive shaft, a first distal worm gear in operable engagement with the first proximal worm gear, and a first drive connector in operable engagement with the first distal worm gear. The first proximal worm gear and the first distal worm gear are configured to rotate the first drive connector at a second speed which is less than the first speed.

In certain aspects of the disclosure, the adapter assembly further includes a second drive assembly. The second drive assembly includes a second connector drive shaft configured to be rotated at a first speed, a second proximal worm gear in operable engagement with the second connector drive shaft, a second distal worm gear in operable engagement with the second proximal worm gear, and a second drive connector in operable engagement with the second distal worm gear. The second proximal worm gear and the second distal worm gear may be configured to rotate the second drive connector at a second speed which is less than the first speed of the second connector drive shaft.

The adapter assembly may include a handle defining a longitudinal axis. Each of the first and second proximal and distal worm gears may define a longitudinal axis. The longitudinal axis of either or both of the first and second proximal worm gears may extend parallel to the longitudinal axis of the handle. The longitudinal axis of either or both of the first and second distal worm gears may extend perpendicular to the longitudinal axis of the handle.

In aspects of the disclosure, the first drive assembly is configured to effectuate cutting of tissue and the second drive assembly is configured to effectuate stapling of tissue. The first drive assembly may include a first pusher assembly having a first pusher member. The first drive assembly may be configured to convert rotational motion of the first drive shaft into longitudinal motion of the first pusher member.

In other aspects of the disclosure, the second drive assembly includes a second pusher assembly having a second pusher member. The second drive assembly may be configured to convert rotational motion of the second drive shaft into longitudinal motion of the second pusher member.

An adapter assembly for operably connecting an end effector to a handle assembly includes a first drive assembly and a second drive assembly. The first drive assembly includes a first proximal worm gear and a first distal worm gear. The first drive assembly may be configured to reduce a speed of rotation from a first input source. The second drive assembly includes a second proximal worm gear and a second distal worm gear. The second drive assembly may be configured to reduce a speed of rotation from a second input source.

In aspects of the disclosure, the adapter assembly includes a handle defining a longitudinal axis. Each of the first and second proximal and distal worm gears may define a longitudinal axis. The longitudinal axis of the first and second proximal worm gears may extend parallel to the longitudinal axis of the handle. The longitudinal axis of the first and second distal worm gears may extend perpendicular to the longitudinal axis of the handle.

In certain aspects of the disclosure, the first drive assembly is configured to effectuate cutting of tissue and the second drive assembly is configured to effectuate stapling of tissue.

BRIEF DESCRIPTION OF THE DRAWINGS

Various aspects and features of the disclosure are described with reference to the drawings wherein like numerals designate identical or corresponding elements in each of the several views, wherein.

DETAILED DESCRIPTION

Figure 1:
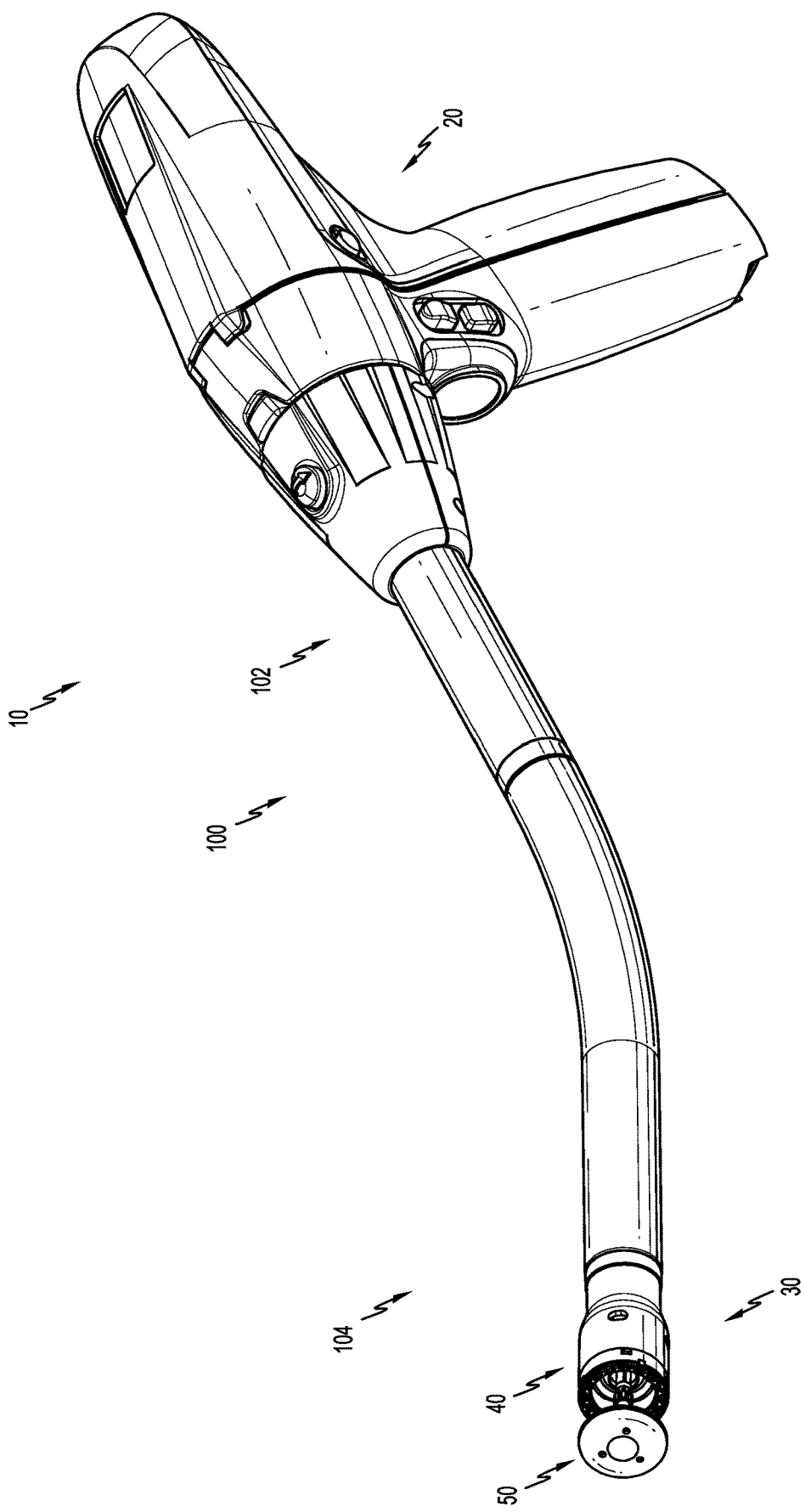
FIG. 1 is a perspective view of an adapter assembly, in accordance with aspects of the disclosure, an exemplary extension assembly, and an exemplary electromechanical surgical device.

Aspects of the disclosed adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

FIG. 1 illustrates an adapter in accordance with aspects of the disclosure, shown generally as adapter 100, as part of a surgical stapling instrument 10. Although shown as being configured for use as a hand-held stapler, it is envisioned that the aspects of the adapter may be modified for use in robotic systems.

The adapter 100 includes an adapter assembly 102 configured for selective connection to a powered handheld electromechanical instrument of the surgical stapling instrument 10, shown generally as handle assembly 20, and an extension assembly 104 configured for connection with a tool assembly or end effector, e.g. tool assembly 30 of the surgical stapling instrument 10, including a loading unit, e.g. loading unit 40, and an anvil assembly, e.g., anvil assembly 50, for applying a circular array of staples (not shown) to tissue (not shown).

The structure and function of the surgical stapling instrument 10 will only be described to the extend necessary to fully disclose the aspects of the disclosure. For a detailed description of the structure and function of an exemplary handle assembly, please refer to U.S. Pat. No. 9,055,943 ("the '943 patent"), the entire content of which being incorporated herein by reference. For a detailed description of the structure and function of an exemplary adapter, including an exemplary adapter and extension assemblies, please refer to U.S. Pat. App. Pub. No. 2017/0128123 ("the '123 application"), the entire content of which being incorporated herein by reference.

Figure 2:
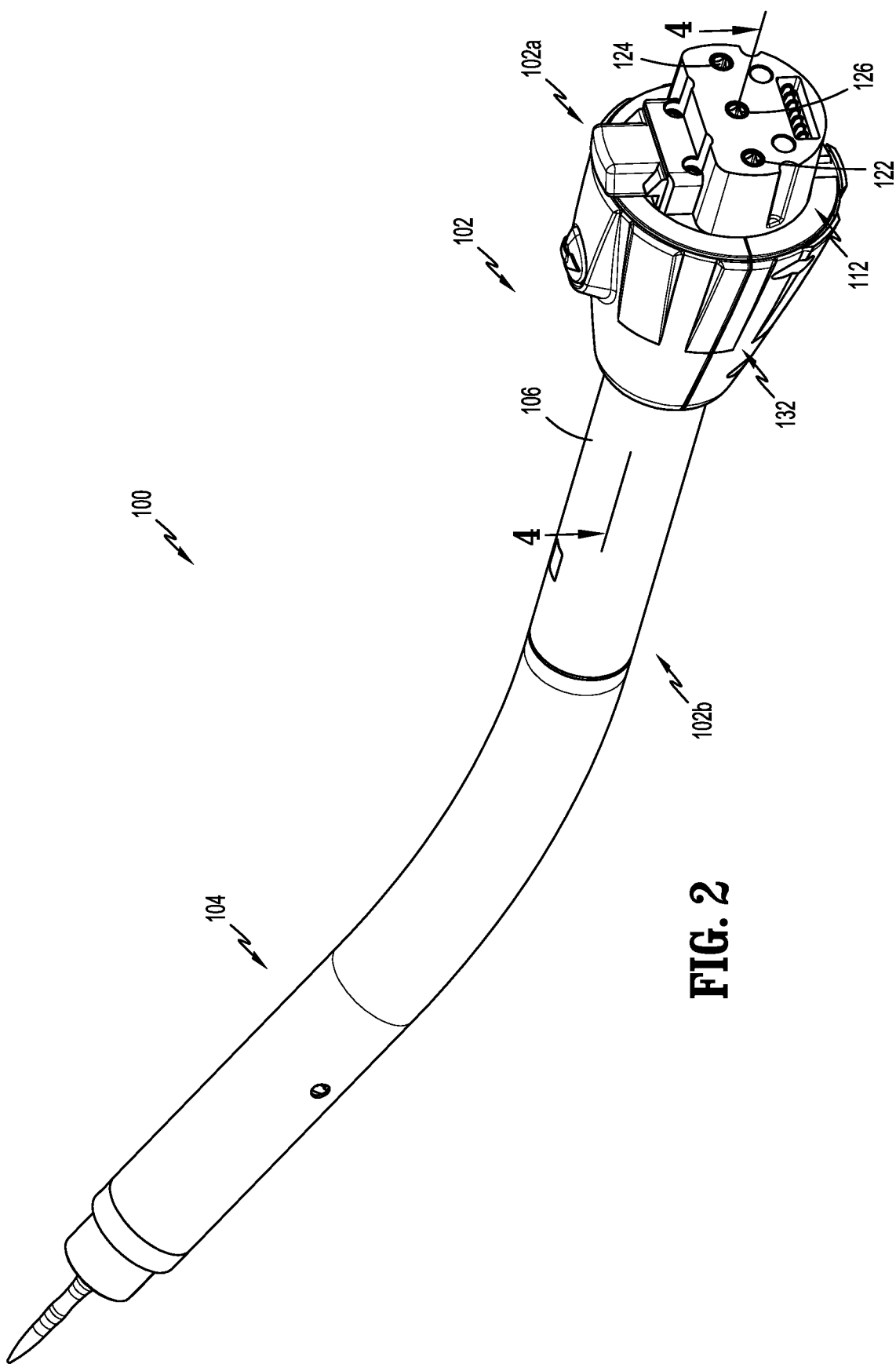
FIG. 2 is a side view of the adapter assembly shown in FIG. 1.

FIG. 2 illustrates the adapter assembly 102 and the extension assembly 104 of the adapter 100 of the surgical stapling instrument 10 (FIG. 1). The adapter assembly 102 includes a proximal portion 102a configured for operable connection to the handle assembly 20 (FIG. 1) and a distal end 102b configured for operable connection to the extension assembly 104 (FIG. 1). The extension assembly 104 will only be described to the extent necessary to fully disclose the aspects of the disclosure. For a detailed description of the structure and function of exemplary extension assemblies, please refer to the '943 patent and the '123 application.

Figure 3:
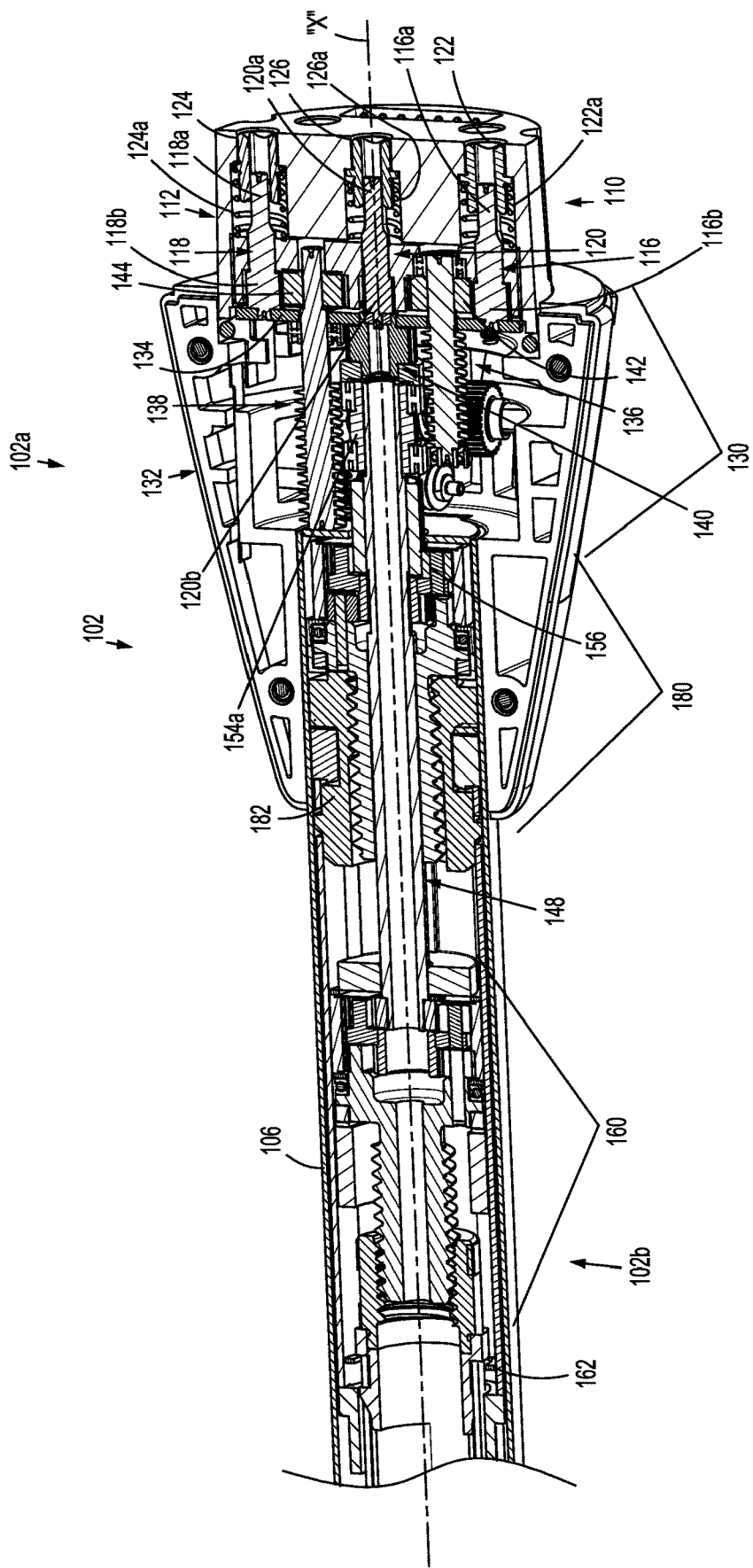
FIG. 3 is a cross-sectional side view of the adapter assembly shown in FIG. 2 taken along section line 3-3 shown in FIG. 2.

FIG. 3 illustrates the internal components of the adapter assembly 102 of the adapter 100 (FIG. 2) of the surgical stapling instrument 10 (FIG. 1). From the proximal portion 102a of the adapter assembly 102 to the distal end 102b of the adapter assembly 102, the adapter assembly 102 includes a drive coupling assembly 110, a drive transfer assembly 130 operably connected to the drive coupling assembly 110, a first pusher assembly 160 operably connected to the drive transfer assembly 130, and a second pusher assembly 180 operably connected to the drive transfer assembly 130. Each of the first and second pusher assemblies 160, 180 are operably maintained within an outer sleeve 106 of the adapter assembly 102 of the adapter 100.

The drive coupling assembly 110 of the adapter assembly 102 includes a cylindrical profile and is configured to selectively secure the adapter 100 to the handle assembly 20 (FIG. 1) of the surgical stapling instrument 10. The drive coupling assembly 110 includes a connector housing 112 rotatably supporting first, second and third connector drive shafts 116, 118, 120, and first, second, and third connector sleeves 122, 124, and 126, respectively, configured to mate with the respective first, second, and third drive connectors (not shown) of the handle assembly 20 of the surgical stapling instrument 10 (FIG. 1). Each of the connector sleeves 122, 124, 126 is further configured to mate with a proximal end 116a, 118a, 120a of respective first, second and third connector drive shafts 116, 118, 120.

The drive coupling assembly 110 also includes first, second and third biasing members 122a, 124a and 126a disposed distally of the respective first, second and third connector sleeves 122, 124, 126. Each of the biasing members 122a, 124a and 126a is disposed about the respective first, second, and third connector drive shafts 122, 124 and 126 to help maintain the connector sleeves 122, 124, and 126 engaged with the distal end of the respective rotatable drive connectors (not shown) of the handle assembly of the surgical stapling instrument 10 when the adapter assembly 102 of the adapter is connected to the surgical stapling instrument 10. In particular, the first, second, and third biasing members 122a, 124a, and 126a function to bias the respective connector sleeves 122, 124, and 126 in a proximal direction.

For additional description of the structure and function of exemplary drive coupling assemblies, please refer to the '943 patent and the '123 application.

The drive transfer assembly 130 is disposed within a handle 132 of the adapter assembly 102. In some aspects of the disclosure, the handle 132 include a frustoconical shape to facilitate engagement by a clinician. The handle 132 is rotatable supported by the connector housing 112 of the drive coupling assembly 110 and fixedly supports the outer sleeve 106 to permit rotation of the outer sleeve 106 of the adapter assembly 102 about a longitudinal axis "X" of the adapter assembly 102 relative to the handle assembly 20 (FIG. 1) of the surgical stapling instrument 10.

The drive transfer assembly 130 includes a support plate 134 for supporting a first proximal worm gear 136, a second proximal worm gear 138, and a drive socket 140. The first and second proximal worm gears 136, 138 are each operably connected to the respective first and second connector drive shafts 116, 118 of the drive coupling assembly 110 by respective first and second proximal drive gears 142, 144. Each of the first and second proximal worm gears 136, 138 defines a longitudinal axis that extends parallel to the longitudinal axis "X" of the adapter assembly 102. The distal end of each of the first and second connector drive shafts 116, 118 include a geared portion 116b, 118b, respectively, which engages the respective first and second proximal drive gears 142, 144 on a proximal end of the respective first and second proximal worm gears 136, 138. Each of the first and second proximal worm gears 136, 138 operates to reduce the output speed and/or increase the torque supplied to the respective first and second connector drive shafts 116, 118 of the coupling assembly 110.

In some aspects of the disclosure, and as shown, each of the respective gear portions 116a, 118a of the respective first and second connector drive shafts 116, 118 include a smaller diameter than the respective first and second proximal drive gears 142, 144, thereby reducing the input speed from the respective first and second connector drive shafts 116, 118. It is envisioned that either or both of the paired geared portions 116a, 118a and first and second proximal drive gears 142, 144 may be of the same size to maintain a 1:1 gear ratio, or of different sizes to alter the gear ratio between the paired gears.

A distal end 120b of the third connector drive shaft 120 of the drive coupling assembly 110 is directly secured to the drive socket 140 of the drive transfer assembly 130. The direct connection between the third connector drive shaft 120 and the drive socket 140 provides a 1:1 gear ratio between the third connector drive shaft 120 and the drive socket 140. In this manner, the third connector drive shaft 120 and the drive socket 140 rotate at the same speed. However, it is envisioned that drive transfer assembly 130 may be modified to permit the addition of gears (not shown) of different sizes and/or configurations to alter the gear ratio between the third connector drive shaft 120 and the drive socket 140. The drive socket 140 is configured to releasably engage a proximal a drive shaft (not shown) of the extension assembly 104 (FIG. 2).

Figure 4:
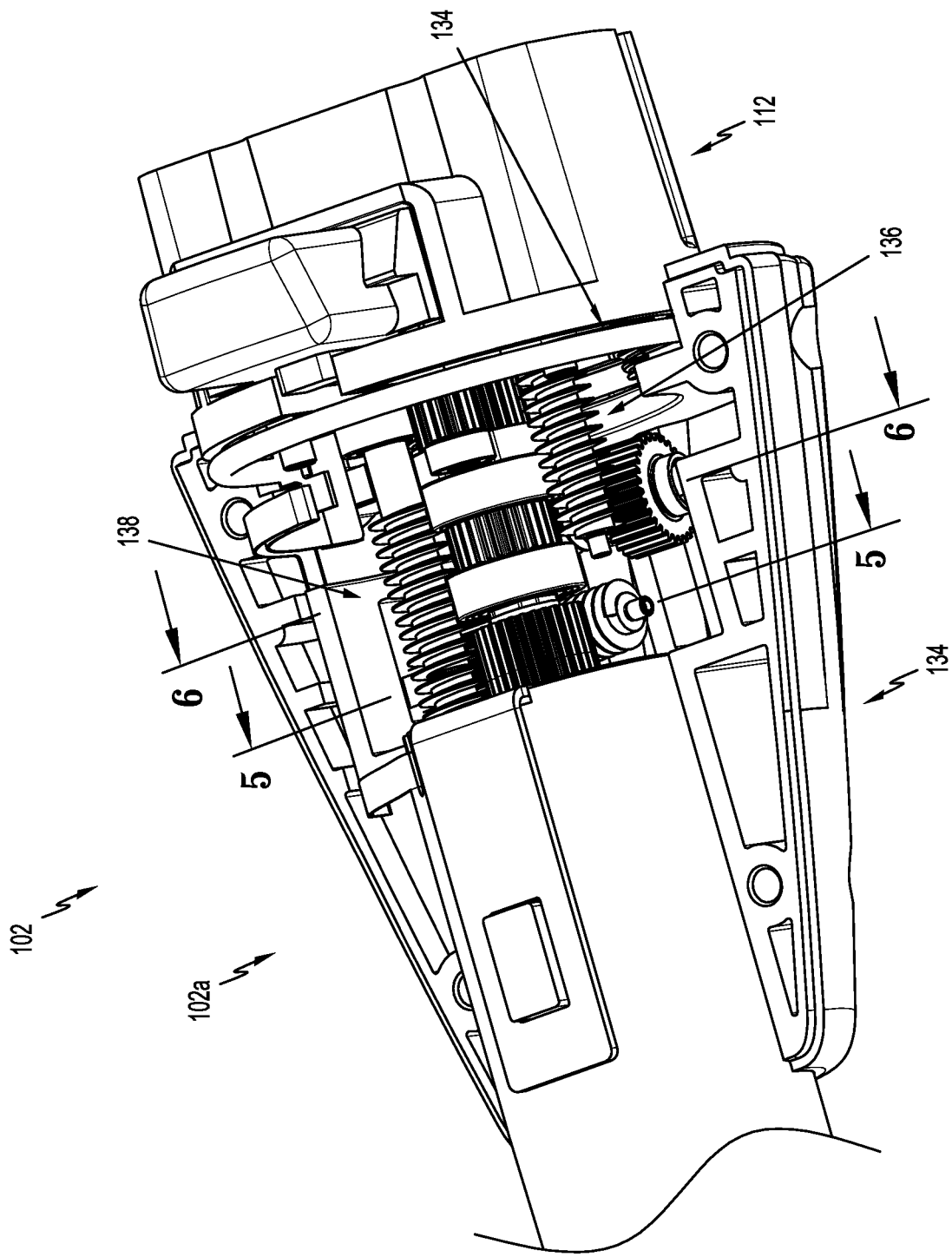
FIG. 4 is a perspective top view of a proximal portion of the adapter assembly shown in FIGS. 2 and 3, with a top half of a handle removed.
Figure 5:
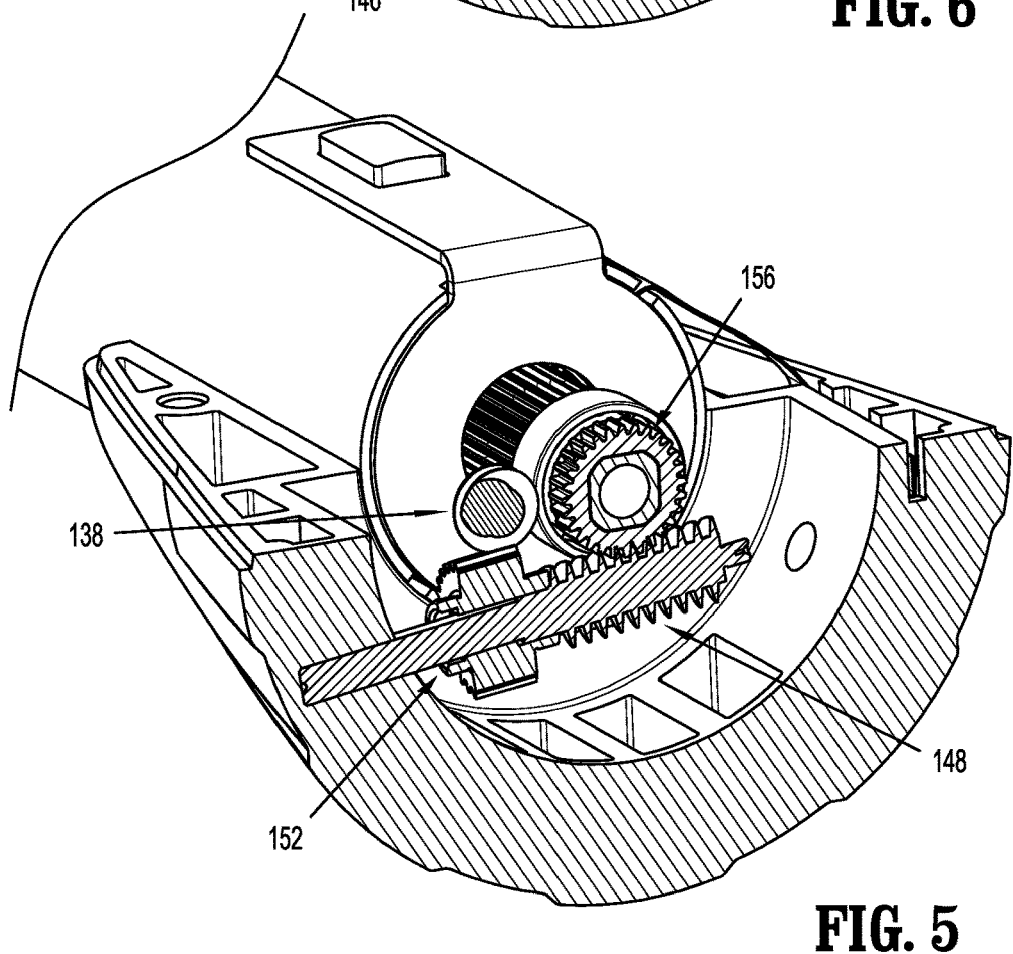
FIG. 5 is a cross-sectional end view of the adapter assembly shown in FIGS. 2-4 taken along section line 5-5 shown in FIG. 4.

FIGS. 4 and 5 illustrate the first proximal worm gear 136 of the drive transfer assembly 130 in operable engagement with a first distal drive gear 150, and the first distal drive gear 150 in operable engagement with a first distal worm gear 146. A geared end 154a of a first drive connector 154 operably engages the first distal worm gear 136 and operably connects the drive transfer assembly 130 to the first pusher assembly 160 (FIG. 3). The first distal worm gear 146 defines a longitudinal axis that extends perpendicular to the longitudinal axis "X" of the adapter assembly 102. The first distal worm gear 146 of the drive transfer assembly 130 operates to further reduce the speed and/or increase the torque supplied to the first connector drive shaft 116 of the coupling assembly 110 by the handle assembly 20 (FIG. 1) of the surgical stapling instrument 10.

The first connector drive shaft 116, the first proximal worm gear 136, the first distal worm gear 146, and each of the first proximal and distal drive gears 142, 150, the first drive connector 154, and the first pusher assembly 160 form a first drive assembly of the adapter assembly 102. The first drive assembly operates to convert rotational motion from the handle assembly 20 (FIG. 1) to longitudinal movement of a first pusher member 162 (FIG. 3) of the first pusher assembly 160. In certain aspects of the disclosure, advancement of the first pusher member 162 causes the cutting of tissue (not shown) disposed between the loading unit 40 (FIG. 1) and the anvil assembly 50.

Figure 6:
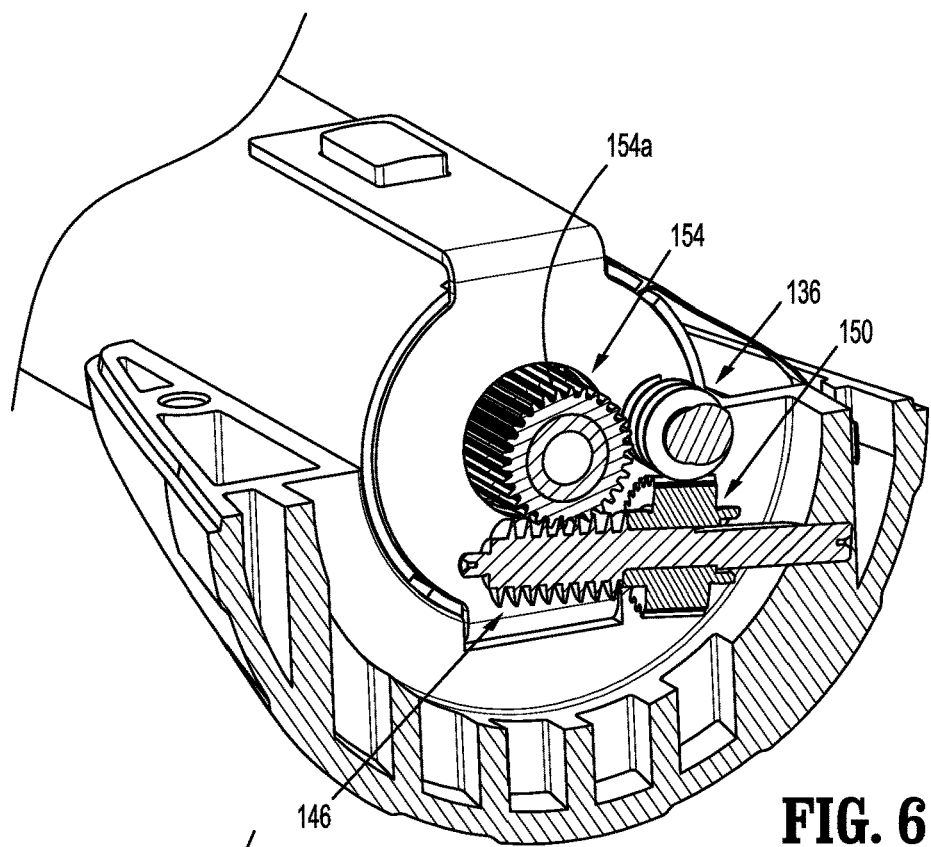
FIG. 6 is a cross-sectional end view of the adapter assembly shown in FIGS. 2-4 taken along section line 6-6 shown in FIG. 4.

FIGS. 4 and 6 illustrate the second proximal worm gear 138 of the drive transfer assembly 130 in operable engagement with a second distal drive gear 152, and the second distal drive gear 152 in operable engagement with a second distal worm gear 148. A second drive connector 156 operably engages the second distal worm gear 136 and operably connects the drive transfer assembly 130 to the second pusher assembly 180 (FIG. 3). The second distal worm gear 148 defines a longitudinal axis that extends perpendicular to the longitudinal axis "X" of the adapter assembly 102. The second distal worm gear 148 of the drive transfer assembly 130 operates to further reduce the input speed and/or increase the torque supplied to the second connector drive shaft 118 (FIG. 3) of the coupling assembly 110 by the handle assembly 20 (FIG. 1) of the surgical stapling instrument 10.

The second connector drive shaft 118, the second proximal worm gear 138, the second distal worm gear 148, and each of the second proximal and distal drive gears 144, 152, the second drive connector 156, and the second pusher assembly 180 form a second drive assembly of the adapter assembly 102. The second drive assembly operates to convert rotational motion from the handle assembly 20 (FIG. 1) to longitudinal movement of a second pusher member 182 (FIG. 3) of the second pusher assembly 180. In certain aspects of the disclosure, advancement of the second pusher member 182 causes the stapling of tissue (not shown) disposed between the loading unit 40 (FIG. 1) and the anvil assembly 50.

The adapter assembly 102 of the adapter 100 (FIG. 2) operably engages the extension assembly 104 of the adapter 100 and the handle assembly 20 (FIG. 1) of the surgical stapling instrument 10 as shown and described in the '123 application. Similarly, the operation of the adapter 100 is similar to that described in the '123 application.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. An adapter assembly for operably connecting an end effector to a handle assembly, the adapter assembly comprising:
   a first drive assembly including:
      a first connector drive shaft configured to be rotated at a first speed,
      a first proximal worm gear in operable engagement with the first connector drive shaft,
      a first distal worm gear in operable engagement with the first proximal worm gear, and
      a first drive connector in operable engagement with the first distal worm gear, wherein the first proximal worm gear and the first distal worm gear are configured to rotate the first drive connector at a second speed, the second speed being less than the first speed.

2. The adapter assembly of claim 1, further comprising:
   a second drive assembly including,
      a second connector drive shaft configured to be rotated at a first speed,
      a second proximal worm gear in operable engagement with the second connector drive shaft,
      a second distal worm gear in operable engagement with the second proximal worm gear, and
      a second drive connector in operable engagement with the second distal worm gear, wherein the second proximal worm gear and the second distal worm gear are configured to rotate the second drive connector at a second speed, the second speed of the second drive connector being less than the first speed of the second connector drive shaft.

3. The adapter assembly of claim 1, further including a handle defining a longitudinal axis, wherein each of the first proximal and distal worm gears define a longitudinal axis, the longitudinal axis of the first proximal worm gear extending parallel to the longitudinal axis of the handle.

4. The adapter assembly of claim 3, wherein the longitudinal axis of the first distal worm gear extends perpendicular to the longitudinal axis of the handle.

5. The adapter assembly of claim 2, further including a handle defining a longitudinal axis, wherein each of the first and second proximal and distal worm gears define a longitudinal axis, the longitudinal axes of the first and second proximal worm gears extending parallel to the longitudinal axis of the handle.

6. The adapter assembly of claim 5, wherein the longitudinal axes of the first and second distal worm gear extend perpendicular to the longitudinal axis of the handle.

7. The adapter assembly of claim 1, wherein the first drive assembly is configured to effectuate cutting of tissue.

8. The adapter assembly of claim 2, wherein the second drive assembly is configured to effectuate stapling of tissue.

9. The adapter assembly of claim 1, wherein the first drive assembly further includes a first pusher assembly including a first pusher member.

10. The adapter assembly of claim 9, wherein the first drive assembly is configured to convert rotational motion of the first drive shaft into longitudinal motion of the first pusher member.

11. The adapter assembly of claim 2, wherein the second drive assembly further includes a second pusher assembly including a second pusher member.

12. The adapter assembly of claim 11, wherein the second drive assembly is configured to convert rotational motion of the second drive shaft into longitudinal motion of the second pusher member.

13. An adapter assembly for operably connecting an end effector to a handle assembly, the adapter assembly comprising:
 a first drive assembly including a first proximal worm gear and a first distal worm gear, the first drive assembly being configured to reduce a speed of rotation from a first input source;
 a second drive assembly including a second proximal worm gear and a second distal worm gear, the second drive assembly being configured to reduce a speed of rotation from a second input source.

14. The adapter assembly of claim 13, further including a handle defining a longitudinal axis, wherein each of the first and second proximal and distal worm gears define a longitudinal axis, the longitudinal axis of the first and second proximal worm gears extending parallel to the longitudinal axis of the handle.

15. The adapter assembly of claim 14, wherein the longitudinal axis of the first and second distal worm gears extend perpendicular to the longitudinal axis of the handle.

16. The adapter assembly of claim 13, wherein the first drive assembly is configured to effectuate cutting of tissue.

17. The adapter assembly of claim 13, wherein the second drive assembly is configured to effectuate stapling of tissue.

18. A surgical instrument comprising:
 a handle assembly;
 an end effector; and
 an adapter assembly for operably connecting the end effector to the handle assembly, the adapter assembly including,
 a first drive assembly including a first proximal worm gear and a first distal worm gear, the first drive assembly being configured to reduce a speed of rotation from a first input source;
 a second drive assembly including a second proximal worm gear and a second distal worm gear, the second drive assembly being configured to reduce a speed of rotation from a second input source.

19. The surgical instrument of claim 18, wherein the first drive assembly is configured to effectuate cutting of tissue.

20. The surgical instrument of claim 19, wherein the second drive assembly is configured to effectuate stapling of tissue.

* * * * *